United States Patent
Burgkart

(10) Patent No.: US 7,950,299 B2
(45) Date of Patent: May 31, 2011

(54) ADJUSTING AND GUIDING SYSTEM FOR TOOLS

(76) Inventor: Rainer Burgkart, München (DE)

( * ) Notice: Subject to any disclaimer, the term of this patent is extended or adjusted under 35 U.S.C. 154(b) by 328 days.

(21) Appl. No.: 12/224,233

(22) PCT Filed: Feb. 21, 2007

(86) PCT No.: PCT/DE2007/000320
§ 371 (c)(1),
(2), (4) Date: Aug. 21, 2008

(87) PCT Pub. No.: WO2007/095917
PCT Pub. Date: Aug. 30, 2007

(65) Prior Publication Data
US 2009/0069945 A1    Mar. 12, 2009

(30) Foreign Application Priority Data

Feb. 21, 2006 (DE) .................. 10 2006 008 398

(51) Int. Cl.
*F16H 21/10* (2006.01)
(52) U.S. Cl. .......................................... 74/1 R
(58) Field of Classification Search ............. 74/1 R; 700/275; 606/62, 88; 343/754, 757
See application file for complete search history.

(56) References Cited

U.S. PATENT DOCUMENTS

| | | | |
|---|---|---|---|
| 6,205,411 | B1 | 3/2001 | DiGioia et al. |
| 6,503,249 | B1 * | 1/2003 | Krause ............................. 606/62 |
| 7,744,600 | B2 * | 6/2010 | Rangaiah et al. ................ 606/88 |
| 2005/0149041 | A1 * | 7/2005 | McGinley et al. ............... 606/88 |
| 2006/0155189 | A1 * | 7/2006 | Lavallee et al. ................ 600/426 |

FOREIGN PATENT DOCUMENTS

| | | |
|---|---|---|
| DE | 20 2005 0011450 | 5/2005 |
| DE | 20 2005 010178 | 10/2005 |

OTHER PUBLICATIONS

International Search Report for PCT/DE2007/000320 dated Aug. 14, 2007.

* cited by examiner

*Primary Examiner* — Vicky A Johnson
(74) *Attorney, Agent, or Firm* — McCracken & Frank LLP

(57) ABSTRACT

The invention relates to an adjusting and guiding system for guiding tools (1) in relation to a workpiece (2), said system comprising the following characteristics: a navigation system (3) used to identify reference points, a first reference point unit (4) that can be fixed to the workpiece (2), a first template receiving element (5) that can be fixed to the workpiece (2), a second reference point unit (6) that can be fixed to the first template receiving element (5), and a template. Said template comprises a coupling part (7a) adapted to the first template receiving element, a tool guiding element (7b) adapted to the tool (2) to be guided, a lockable coupling device (7c) connecting the coupling part (7a) to the tool guiding element (7b) and enabling the tool guiding element (7b) to be oriented in relation to the coupling piece (7a), and a template adjusting device (8). Said template adjusting device is characterized by a second template receiving element (8a) connected to the template adjustment device (8) in a geometric relation therewith, the first and the second template receiving elements being identical, a tool guiding coupling (8b) for the defined connection of the tool guiding element (7b) of the template to the template adjustment device (8), and an adjusting device (8c) comprising adjusting elements that can be displaced in a defined manner and are used for the defined orientation of the tool guiding coupling (8b), said adjusting elements (8c) being provided with measuring scales.

20 Claims, 3 Drawing Sheets

FIG. 1
axis-related guidance of the tool
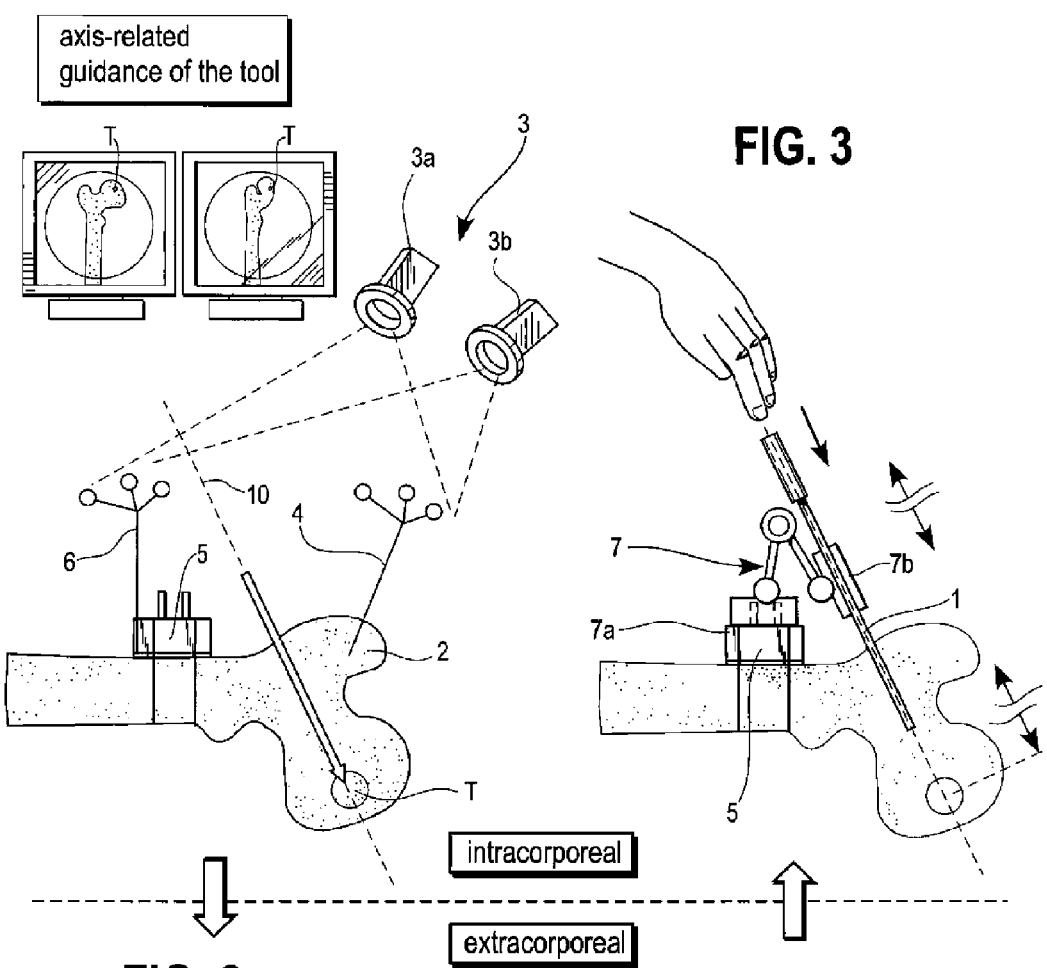
intracorporeal
extracorporeal
FIG. 2a
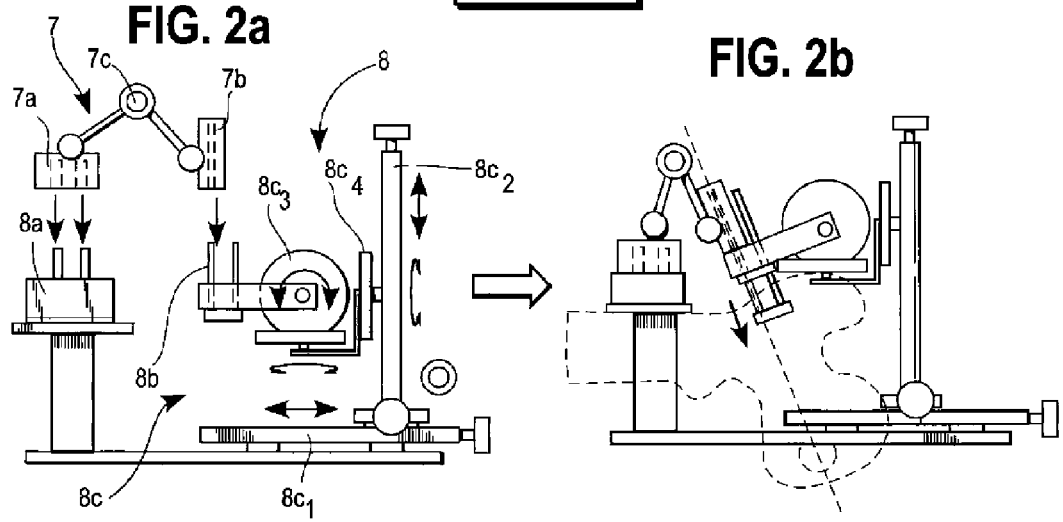
FIG. 2b
FIG. 3

ADJUSTING AND GUIDING SYSTEM FOR TOOLS

BACKGROUND

Various techniques are known from the state of the art for making bores, counter-sinking or saw cuts with a predetermined spatial orientation and depth. One known technique is the marking of the work piece with a point or line, whereby the point can be the middle point of a bore and the line can be the course of a saw cut.

In order to be able to introduce predetermined recesses into a work piece, fundamentally the required geometric relationships between the work piece and the tools have to be established. For example, if a centered work piece is fastened in a vice that lies freely displaceably on the table of an upright drill, the vice must be adjusted by the worker with one hand so that the bore tip lies exactly above the center point. The worker then operates the lever with the other hand to lower the drill spindle, in order to bore the intended hole. When the hole must have a predetermined depth, the worker will observe the scale provided on the drill spindle from which he can determine the extent of the lowering of the drill.

In order to provide the same work piece with the same bore, one can consider the use of a robot drill, which is equipped with an image recognition device that recognizes the position of the work piece automatically so that, with the aid of a computer program, one can determine how the robot head with the bore is to be directed and guided.

However, there are cases of application in which measurement technological access to the "work piece" to be worked on is difficult. Thus, for example it may be necessary to take a sample from an archeological find, for example from a mummy. Without extensive explanation of the necessity, let us presume that hereby the mummy may be opened only minimally.

In order to solve this task, one can use the so-called navigation system known from medical technology. This is a system with a navigation camera, which is able to recognize reference points in the room. If such reference points are attached to the tool and the work piece (in the medical area, on a part of the body) then, with the aid of the computer assigned to the camera, the spatial relationship between the work piece and the tool can be established. It is clear to the expert in the field that for this purpose the geometry of the tool and the work piece and the position of the reference point with respect to the tool and the work piece must be known. These working steps are sufficiently known because they can be taken from the operating procedures of the navigation systems. In order to produce a bore, it is thus possible to represent the work piece together with the tool on the provided virtual bore axis on a screen. The drill is now guided by hand so that its spatial position and its forward movement (drill feed movement) coincide with the virtual bore axis. Hereby the operator must look at the monitor that is away from the actual relevant working area, to align and move the tool until the actual position and the target position are identical. This hand-eye coordination is stressful and presumes good spatial imagination and much training.

This technique is described in documents U.S. Pat. No. 6,226,548; U.S. Pat. No. 6,747,646; U.S. Pat. No. 6,725,080; U.S. Pat. No. 6,697,664; U.S. Pat. No. 6,535,756; U.S. Pat. No. 6,470,207; U.S. Pat. No. 6,205,411. In addition to the most frequently used optical navigation cameras, the position and orientation recognition can also be performed using ultrasound-based or electromagnetic detection methods, among others, as described, for example, in the document U.S. Pat. No. 6,503,249. However, the basic principles outlined above are identical.

In order to relieve the person performing the job (worker or operator), called operator below, from the difficult hand-eye coordination, there is the possibility of using mechanical calibers that guide the tool mechanically, for example the drill or the saw blade, so that he operator has to perform only one movement, for example with one single degree of freedom. The difficulty in this technique consists in the aligning and fixing of the mechanical caliber in the correct geometrical position with respect to the work piece or with respect to the body part to be worked on. In principle, this is possible with a robot described in document U.S. Pat. No. 6,837,892 in combination with a navigation system.

However, there are cases of application in which a robot is not suitable due to its size (unwieldiness), its weight and its mechanical sensitivity. Such cases occur in the medical as well as in the non-medical area. For example, it is clear to the person skilled in the art that such a robot is not very suitable, for example, when a mummy is to be investigated which is located in the crypt of a pyramid or when a medical operation must be performed on a living human and a cumbersome robot is to be kept sterile.

Therefore, the task of the invention is to provide a technique for guiding a tool that makes guiding of the tool possible, for example, in the sense of a drill caliber or an installation for applying a saw. Hereby the tool should be directed by a tool guiding element in such a way that the tool penetrates into the work piece in the intended spatial orientation.

SUMMARY

This task is solved with an adjusting and guiding system according to claim 1. The adjusting and guiding system according to the invention has several components including, in one embodiment, a navigation system, a first reference point unit, a first template receiving element, a second reference point unit, a template, and a template adjustment device. In another embodiment of the invention, an adjusting and guiding system for mechanical guidance of a surgical tool with respect to a work piece includes a first template receiving element adapted to be attached to the work piece, and a reference point unit, a navigation system adapted to recognize and track a position of the reference point unit with respect to the position of the work piece, a template for guiding the surgical tool, and an adjustment device for adjusting the template into a spatial alignment defined by the navigation system. In addition, advantageous embodiments of the invention are objects of the subclaims.

The invention will be explained in more detail below with the aid of the attached drawings for a medical case of application:

BRIEF DESCRIPTION OF THE DRAWINGS

FIG. 1 shows a bone with a tumor to be removed.

FIG. 2*a*V shows an enlarged image of FIG. 2*a*

FIG. 2*b* shows a part of the invention from FIG. 2*a* in the mounted state.

FIG. 3 shows a part of the invention used in the bone for the removal of the tumor.

DETAILED DESCRIPTION

Figure 2A:
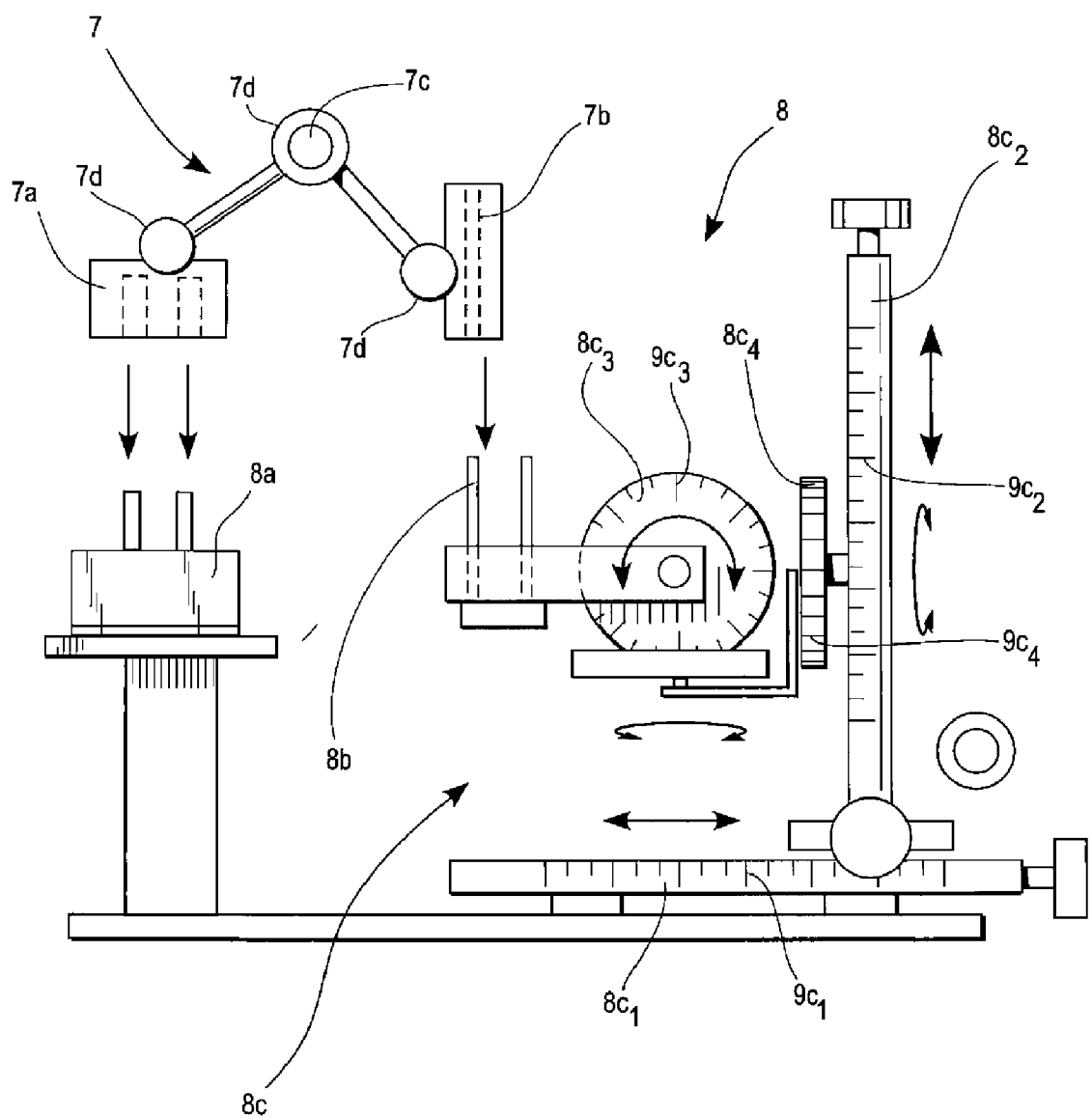
FIG. 2*a* shows an essential part of the invention.

A system according to one embodiment includes a navigation system 3 with which reference points in the room can be recognized without contact. A typical embodiment of a navigation system operates according to the optical principle, that is, an optical system, consisting of two cameras $3a$, $3b$, detects reference points and assigns these reference points spatially to one another, which is converted with a computer with the corresponding software. This process is called tracking in the state of the art. The reference points are mostly combined into a reference point unit, whereby a rod-shaped carrier carries at least three reference points that have a predetermined distance to one another. The reference points are material spheres made of a material that is recognized by the cameras when the reference points are illuminated with a certain light source, mostly infrared.

A first reference point unit 4 is attached to the work piece. Then images of the work piece are produced from different perspectives. These can be for example x-ray recordings. With the fixing of the photographic recordings on the work piece and on the related photographic recordings, for example, x-ray recordings from different directions, a spatial assignment between the previously-determined, that is, known, work piece geometry and the known geometry of the reference point unit is established and stored in the computer of the navigation system. When the navigation system recognizes the reference point unit thus at the same time the spatial position of the work piece is known.

It is clear to the person skilled in the art that the reference point unit 4 does not necessarily have to be attached to the work piece itself. It is sufficient if a fixed relationship is established between the work piece and the reference point unit. Such a fixed relationship is produced for example when the work piece is clamped rigidly in a vice and the reference point unit is connected solidly to the vice.

This principle can also be transferred to a medical application, that is, when, for example, a leg on which a surgery is to be performed is sufficiently fixed then the first reference point unit 4 can also be secured next to the leg, as long as it is guaranteed that the position of the leg, that is of the bone, is not changed with respect to this first reference point unit.

Now a device is secured on the work piece, which will be called the first template receiving element 5 below. This template receiving element carries the second reference point unit 6.

Furthermore, a device is used, which will be called template 7 below and which has the following characteristics: a coupling part 7a, which fits with positive locking and unequivocally to the first template receiving element. The coupling part is thus a body section of the template.

The template 7 also has a mechanical tool guiding element 7b, which fits the tool to be guided. For example, when a drill is to be guided, the tool guiding element has a sleeve with a bore that corresponds to the drill diameter. When a saw is to be guided, the tool guiding element 7b is designed so that the saw blade is guided, that is, can be applied, at least by one side on a line.

The coupling part 7a and the tool guiding element 7b are connected to one another with a coupling device 7c. The coupling device 7c has joints so that a predetermined spatial alignment of the tool guiding element 7b with respect to the coupling part 7a is made possible. The joints can be set.

In order to obtain an alignment of the tool guiding element 7b with regard to the coupling part 7a, a template adjustment device 8 is used which has the following characteristics: a second template receiving element 8a, which is identical to the first template receiving element 5, that is, the coupling part 7a of the template fits both the first as well as the second template receiving element. The second template receiving element 8a is connected rigidly to the template adjustment device 8 and thus it is in a predetermined geometric relationship to it.

Furthermore, a tool guiding coupling 8b is provided on the template adjustment device 8 which makes it possible to establish a spatially defined connection of the tool guiding element 7b of the template with the template adjustment device.

The tool guiding coupling 8b is attached to an adjusting device 8c, which is also arranged in a fixed manner on the template adjustment device. This adjustment device has at least as many degrees of freedom as required. Thus, with the displaceable adjusting elements $8c_1$, $8c_2$, $8c_3$, and $8c_4$, a spatially defined alignment to the tool guiding coupling is made possible.

Measuring scales are set up on the adjusting elements $8c_1$-$8c_4$ to obtain defined settability, that is, longitudinal scales $9c_1$ and $9c_2$ are provided for shifting in the coordinate system and angle scales $9c_3$ and $9c_4$ are provided for rotations in the coordinate system.

As determined, the adjusting and guiding system is used as follows: the goal is for the mechanical guidance with the tool of the template to be in the correct spatial position for guiding the tool 1 when the template 7 is set on the first template receiving element 5. For this purpose, the coupling part 7a of the template is to be brought into a predetermined spatial position with respect to the tool guiding element 7b, which is possible with the aid of the coupling device 7c that can be set and arrested. The spatial position that corresponds to the desired action of the tool 1 is set with the adjusting elements $8c_1$-$8c_4$. For this purpose, scales $9c_1$-$9c_4$ with numerical values are arranged on the adjusting elements $8c_1$-$8c_4$ so that predetermined length and angle settings can be ensured. The numerical values are calculated with consideration of the geometry of the template 7 and of the template adjustment device 8 in the sense of a 3D transformation.

After the template 7 is set and arrested, it is removed from the template adjustment device 8 and set on the first template receiving element 5 and secured there. Now the operator can produce a bore in the work piece with his tool 1, for example a drill, which he pushes through the tool guiding element 7b, which has the originally planned spatial position.

The preparatory steps before the use of the adjusting and guiding system for the mechanical guidance of tools according to the invention are carried out according to the known procedures of the commercial navigation systems 3. Typically, hereby, stable fixation of a first reference point unit 4 on the patient's bone 2 to be operated on is carried out after the setting up of the navigation system 3 and the alignment of the camera unit $3a$, $3b$ onto the surgical field. Finally, intraoperative image data (for example in the form of fluoroscopy recordings with a tracked calibrated x-ray C-sheet are recorded) or image-free geometrical data of the patient are obtained or preoperatively established image data (for example CT scans) are referenced with the aid of various known matching methods with the actual position of the patient. In this way the work piece data, that is, the bone data, are available on the computer-aided navigation control unit, and the operator can plan his action based on these. For example, if an x-ray C-sheet is used, mostly two recordings of the surgical area are made from 2 different directions that are shown in FIG. 1. After the bone tumor T, which cannot be seen directly in either of the recordings, is marked, its exact spatial position can be calculated inversely with known computing methods (Brack 1998, among others).

After the establishment of the target location T, the operator also establishes the route of access 10 to this target in the sense of a target axis, whereby the arrow in FIG. 1 represents the virtual planning of the direction of penetration of the axis-related tool and the tip of the arrow shows the endpoint of the tip of the tool, that is, the point that the drill must reach.

Now a trackable second reference point unit 6 together with a template receiving element 5 is attached reversibly to a bone section near the surgical field with the aid of screws, clamps or Kirschner wires. After stable fixation of the template receiving element 5, this process is confirmed to be completed by the navigation system.

Now the adjustment of the bone template 7 in a template receiving element 8a is performed. Using a deposited computing algorithm that takes into consideration the geometry of the adjusting device 8, a maximum of 6 numerical values (3 translation values and 3 rotation values), corresponding to the plan are now calculated and outputted.

With the aid of these values, the mechanical tool guiding element 7b on the tool guidance coupling 8b is exactly and unequivocally aligned spatially on the adjusting elements 8c of the adjusting device 8, whereby the arresting elements 7d of the template 7 are released. After that the templates are fixed by means of the arresting elements 7d and are removed from the template adjustment device 8 and placed on the template receiving element 5. It is clear to the person skilled in the art that the adjusting elements 8c can also be arranged on the second template receiving element 8a or some of these can be arranged thus. The only essential thing is that within the template adjustment device 8 the geometrical relationships are known and are adjustable. The second reference point unit 6 is no longer needed and can be removed. Now the operator can set the drill by using the tool guiding element 7b and introduce the bore. It is additionally clear to the expert in the field that the tool guiding element 7b can also be a slit-like recess with which a saw cut can be introduced into the work piece with a predetermined spatial alignment and depth.

Figure 4:
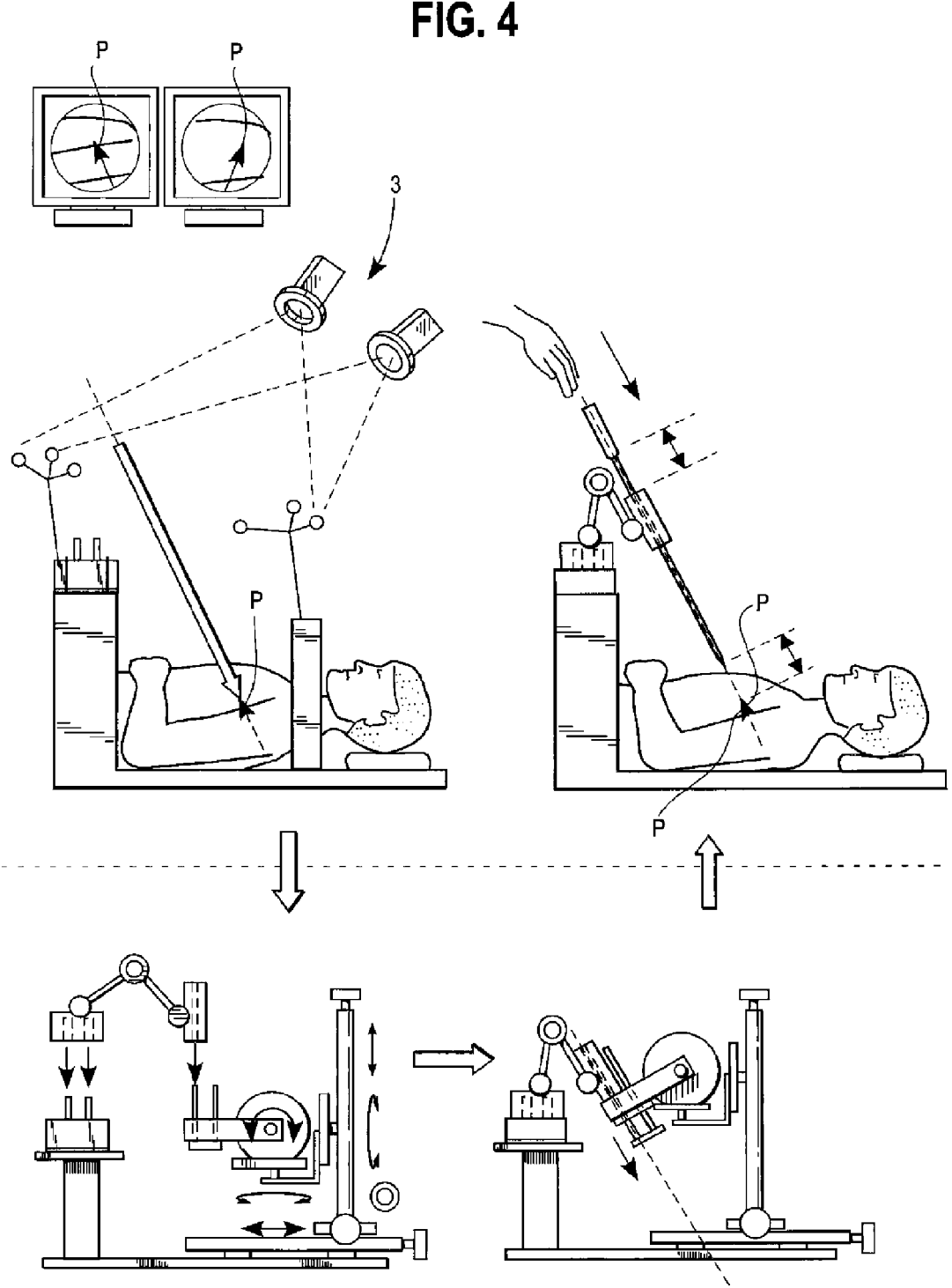
FIG. 4 shows a part of the invention used in a mummy for the removal of an arrow-tip from the lung.

FIG. 4 shows a similar task to that shown in FIGS. 1-3. In the case of a mummy, an arrow tip P was discovered from an x-ray recording in the lung and this is to be removed with a minimally invasive action. Similarly a bore must be planned through which the arrow tip can be removed.

I claim:

1. An adjusting and guiding system for mechanical guiding of tools with respect to a work piece, wherein the adjusting and guiding system comprises:
   a navigation system with which reference points in the room can be recognized without contact;
   a first reference point unit which can be secured on the work piece;
   a first template receiving element which can be secured on the work piece;
   a second reference point unit which can be secured on the first template receiving element;
   a template comprising a coupling piece which fits the first template receiving element, a mechanical tool guiding element which fits the tool to be guided, and an arrestable coupling device which joins the coupling piece to the mechanical tool guiding element and which makes possible selective spatial alignment of the tool guiding element with respect to the coupling piece; and
   a template adjustment device comprising a body and a second template receiving element which is connected to the body in a predetermined geometric relationship thereto, wherein the first and second template receiving elements are identical to one another, a tool guiding coupling for spatially defined joining of the mechanical tool guiding element of the template to the template adjustment device, and an adjusting device with adjusting elements that can be displaced in a defined manner for spatially defined adjustment of alignment of the tool guiding coupling relative to the second template receiving element, wherein measuring scales are provided on the adjusting elements for measuring the defined adjustment of alignment.

2. An adjusting and guiding system according to claim 1, wherein the navigation system is an optical camera system.

3. An adjusting and guiding system according to claim 1, wherein the navigation system is an ultrasound-based system.

4. An adjusting and guiding system according to claim 1, wherein the navigation system has an electromagnetic detection principle.

5. The adjusting and guiding system of claim 1, wherein the coupling piece is releasably attachable to the first template receiving element and the second template receiving device in alternating succession.

6. The adjusting and guiding system of claim 5, wherein the mechanical tool guiding element is attachable to the tool guiding coupling when the coupling piece is attached to the second template receiving device.

7. The adjusting and guiding system of claim 6, wherein the arrestable coupling device comprises joints for allowing adjustment of spatial alignment of the mechanical tool guiding element with respect to the coupling piece and arresting elements for releasably locking the joints.

8. The adjusting and guiding system of claim 1, wherein the measuring scales include longitudinal scales for measuring shifting of the adjusting elements and angle scales for measuring rotations of the adjusting elements.

9. An adjusting and guiding system for mechanical guidance of a surgical tool with respect to a work piece, the system comprising:
   a first template receiving element adapted to be attached to the work piece in a fixed position thereto, and a reference point unit in a fixed position to the first template receiving element;
   a navigation system adapted to recognize and track a position of the reference point unit with respect to the position of the work piece and to identify a planned trajectory of the surgical tool into the work piece relative to the first template receiving element;
   a template for guiding the surgical tool, the template comprising a tool guiding element connected to a coupling part by an arrestable coupling device, wherein the coupling part is releasably lockable to the first template receiving element, wherein the tool guiding element provides a defined guide surface for guiding the surgical tool, and wherein the arrestable coupling device allows lockable adjustment of spatial alignment of the tool guiding element with respect to the coupling part; and
   a template adjustment device for adjusting the template into a spatial alignment defined by the navigation system to meet the planned trajectory, the template adjustment device comprising a second template receiving element, a tool guide coupling, and an adjusting device, wherein the second template receiving element is releasably attachable to the coupling part, the tool guide coupling is releasably attachable to the tool guiding element, and the adjusting device provides for controlled adjustment of spatial alignment of the coupling part and the tool guiding element when attached to the respective second template receiving element and tool guide coupling.

10. The adjusting and guiding system of claim 9, wherein the adjusting device comprises measuring scales for measuring adjustment of the relative spatial alignment between the second template receiving element and the tool guide coupling.

11. The adjusting and guiding system of claim 10, wherein the measuring scales comprise a longitudinal scale for measuring shifting and an angle scale for measuring rotation.

12. The adjusting and guiding system of claim 9, wherein the coupling part attaches alternatingly to each of the first template receiving element and the second template receiving element in the same relative orientation thereto.

13. The adjusting and guiding system of claim 12, wherein the first template receiving element is substantially identical to the second template receiving element.

14. The adjusting and guiding system of claim 9, wherein the navigation system comprises a plurality of cameras and the reference point unit comprise reference markers that are optically visible to the cameras.

15. The adjusting and guiding system of claim 9, wherein the tool guiding element comprises a drill guide.

16. The adjusting and guiding system of claim 9, wherein the tool guiding element comprises a saw guide having a slit-like recess.

17. The adjusting and guiding system of claim 9, further comprising a second reference point unit adapted to be connected directly to the work piece separate from the first template receiving element.

18. The adjusting and guiding system of claim 9, wherein the arrestable coupling device comprises one or more joints and one or more arresting elements for setting the joints in a selected position.

19. The adjusting and guiding system of claim 9, wherein the geometrical relationship between the second template receiving element and the tool guide coupling are known and measured by the measuring scales.

20. The adjusting and guiding system of claim 9, wherein the reference point unit is attached to the first template receiving element.

* * * * *